United States Patent
Burgermeister et al.

(10) Patent No.: US 7,842,312 B2
(45) Date of Patent: Nov. 30, 2010

(54) POLYMERIC COMPOSITIONS COMPRISING THERAPEUTIC AGENTS IN CRYSTALLINE PHASES, AND METHODS OF FORMING THE SAME

(75) Inventors: Robert Burgermeister, Bridgewater, NJ (US); Vipul Dave, Hillsborough, NJ (US)

(73) Assignee: Cordis Corporation, Miami Lakes, FL (US)

( * ) Notice: Subject to any disclaimer, the term of this patent is extended or adjusted under 35 U.S.C. 154(b) by 1231 days.

(21) Appl. No.: 11/321,255

(22) Filed: Dec. 29, 2005

(65) Prior Publication Data

US 2007/0154554 A1    Jul. 5, 2007

(51) Int. Cl.
*A61K 9/50* (2006.01)
(52) U.S. Cl. .................. 424/501; 977/904; 977/906

(58) Field of Classification Search .................. None
See application file for complete search history.

(56) References Cited

U.S. PATENT DOCUMENTS

| 3,929,992 A | 12/1975 | Seghal, et al. |
| 2003/0125800 A1 | 7/2003 | Shulze et al. |

FOREIGN PATENT DOCUMENTS

| EP | 1362602 A1 | 11/2003 |
| EP | 1721625 A | 11/2006 |
| EP | 1723976 A1 | 11/2006 |
| WO | WO 99/21908 A | 5/1999 |

*Primary Examiner*—Carlos A Azpuru

(57) ABSTRACT

The present invention relates to a drug-containing polymeric composition comprising at least one therapeutic agent encapsulated in at least one biocompatible polymer, wherein at least a portion of the therapeutic agent in this polymeric composition is crystalline. The at least one biocompatible polymer may form a substantially continuous polymeric matrix with the at least one therapeutic agent encapsulated therein. Alternatively, the at least one biocompatible polymer may form polymeric particles with the at least one therapeutic agent encapsulated therein.

1 Claim, No Drawings

POLYMERIC COMPOSITIONS COMPRISING THERAPEUTIC AGENTS IN CRYSTALLINE PHASES, AND METHODS OF FORMING THE SAME

FIELD OF THE INVENTION

The present invention relates to polymeric compositions that can be used for sustained and controlled drug delivery. More specifically, the present invention relates to polymeric compositions that each contains at least one therapeutic agent encapsulated in at least one biocompatible polymer, while at least a portion of the therapeutic agent in such polymeric compositions is crystalline.

BACKGROUND OF THE INVENTION

In recent years, drug-eluting implantable medical devices, such as, for example, stents, stent grafts, anastomosis devices, vascular grafts, vascular patches, AV shunts, catheters, guide wires, balloons, and filters, have gained more and more acceptance in the medical device industry as an effective means for controlled and sustained local drug delivery. These implantable medical devices, or at least portions thereof, are typically formed of or coated by a biocompatible polymer (either biostable or biodegradable) that encapsulates or otherwise contains one or more therapeutic drugs. In this manner, the therapeutic drugs are confined in or on the surface of the implantable medical devices by the biocompatible polymer and can be slowly released into the surrounding environment in a controlled and sustained manner.

Injectable formulations that contain drug-eluting nano-particles and/or micro-particles have also been successfully used for controlled and sustained local drug delivery. These nano-particles and/or micro-particles are formed by at least one biocompatible polymer with at least one therapeutic agents encapsulated therein.

The biocompatible polymer is preferably biodegradable, but it can also be biostable. After injecting the nano- and/or micro-particles into a target site in the body, the encapsulated therapeutic drugs are released from the particle surfaces in a controlled and sustained manner, thereby achieving a prolonged and high local drug concentration at or near the target site.

Stability of the therapeutic drugs contained by the above-described implantable devices or nano/micro-particulate formulations has a significant impact on the drug release kinetics of such devices or formulations. In other words, the drug release kinetics may vary widely, depending on the stability of the therapeutic drugs contained therein.

There is therefore a need for improved drug-containing polymeric compositions with improved drug stability, which are suitable for forming drug-eluting implantable medical devices or drug-eluting nano- and/or micro-particulate formulations.

SUMMARY OF THE INVENTION

The present invention in one aspect relates to a drug-containing polymeric composition comprising at least one therapeutic agent encapsulated in at least one biocompatible polymer, wherein at least a portion of the therapeutic agent in such a polymeric composition is crystalline.

The term "polymer" or "polymeric" as used herein refers to any material, composition, structure, or article that comprises one or more polymers, which can be homopolymers, copolymers, or polymer blends.

The term "biocompatible" as used herein refers to any material, composition, structure, or article that have essentially no toxic or injurious impact on the living tissues or living systems which the material, composition, structure, or article is in contact with and produce essentially no immunological response in such living tissues or living systems. More particularly, the material, composition, structure, or article has essentially no adverse impact on the growth and any other desired characteristics of the cells of the living tissues or living systems that are in contact with the material, composition, structure, or article. Generally, the methods for testing the biocompatibility of a material, composition, structure, or article is well known in the art.

Preferably, at least 10% of the therapeutic agent in the polymeric composition of the present invention is crystalline. More preferably, at least 50% of the therapeutic agent in the polymeric composition of the present invention is crystalline. Most preferably, at least 90%, 95%, or 98% of the therapeutic agent in the polymeric composition is crystalline.

In another aspect, the present invention relates to a method for forming a drug-containing polymeric composition, comprising:

forming crystalline particles of at least one therapeutic agent; and encapsulating the crystalline particles into at least one biocompatible polymer to form a drug-containing polymeric composition, wherein at least a portion of the crystalline particles remain crystalline in the drug-containing polymeric composition.

In a further aspect, the present invention relates to a method for forming a drug-containing polymeric composition, comprising:

forming a precursor composition comprising at least one therapeutic agent encapsulated in at least one biocompatible polymer, wherein the at least one therapeutic agent is amorphous;

annealing the precursor composition; and slowly cooling the annealed precursor composition so as to form a drug-containing polymeric composition with at least a portion of the therapeutic agent contained therein being crystalline.

Other aspects, features and advantages of the invention will be more fully apparent from the ensuing disclosure and appended claims.

DETAILED DESCRIPTION OF THE INVENTION, AND PREFERRED EMBODIMENTS THEREOF

In the following description, numerous specific details are set forth, such as particular materials, compositions, formula, structures, devices, and methods for fabricating or using same, in order to provide a thorough understanding of the present invention. However, it will be appreciated by one of ordinary skill in the art that the invention may be practiced without these specific details. In other instances, well-known materials, structures or processing steps have not been described in detail in order to avoid obscuring the invention.

While specific embodiments of the present invention are described and illustrated hereinabove, it is clear that a person ordinarily skilled in the art can readily modify such specific embodiments consistent with the descriptions provided herein. It should therefore be recognized that the present invention is not limited to the specific embodiments illustrated hereinabove, but rather extends in utility to any other modification, variation, application, and embodiment, and accordingly all such other modifications, variations, applications, and embodiments are to be regarded as being within the spirit and scope of the invention.

Drug-containing polymeric compositions have been used recently in forming various implantable medical devices and injectable drug formulations for sustained and controlled local delivery of therapeutic agents. These drug-containing polymeric compositions are typically formed by dissolving one or more therapeutic agents and one or more biocompatible polymers in one or more solvents, followed by removing the solvents to form a solidified drug-containing polymeric composition. The solvent removal or solidification can be carried out using various techniques, including, but not limited to: spray drying (for preparation of coatings), solvent casting or spin coating (for preparation of thin films or membranes), and spinning (for preparation of fibers).

The solidified drug-containing polymeric compositions so formed typically contain the therapeutic agents in an amorphous phase.

However, amorphous therapeutic agents are very unstable, especially at temperatures that are above their glass transition temperatures. The amorphous therapeutic agents may gradually degrade over time, due to oxidation in the presence of oxygen. Such amorphous therapeutic agents can also become plasticized during device sterilization processes.

Therefore, the present invention provides improved drug-containing polymeric compositions that contain the therapeutic agents, or at least a portion thereof, in the more stable crystalline phase.

Preferably, but not necessarily, the drug-containing polymeric compositions of the present invention contain little or no amorphous therapeutic agents, i.e., a major portion (i.e., >50%) of the therapeutic agents contained in such compositions are in the stable crystalline phase. For example, the drug-containing polymeric compositions of the present invention each comprises at least one therapeutic agent encapsulated in at least one biocompatible polymer, while more than 75% of the therapeutic agent in the composition is crystalline. More preferably, more than 90% or more than 95% of the therapeutic agent in the composition is crystalline. Most preferably, the composition is essentially free of amorphous therapeutic agent.

Preferably, but not necessarily, the at least one therapeutic agent used in the present invention is a potent anti-inflammatory and anti-neoplastic agent, such as, for example, rapamycin, rapamycin ester, everolimus, zotarolimus (formerly known as ABT-578), biolimus, tacrolimus, pimecrolimus, wortmannin, taxanes such as paclitaxel, docetaxel, camptothecin, estradiol, Panzem, morphine, epothilone, matrix metalloproteinase (MMP) inhibitor such as tetracycline, cladribine, tranilast, sabeluzole, and their associated derivatives and analogs. Such an anti-inflammatory and anti-neoplastic agent can effectively eliminate neointimal growth post an angioplasty procedure and therefore can be used to prevent or treat restenosis-induced vascular diseases, such as restenosis, vulnerable plaque, aneurysm, and/or stroke. Any other suitable therapeutic agents can also be used in the present invention for treatment of other diseases or conditions. Large molecular weight entities, such as proteins, polypeptides, plasmids, DNAs, RNAs, ribozymes, DNases, siRNAs, anti-sense drugs, etc., can all be formulated according to the present invention.

In a preferred but not necessary embodiment of the present invention, the drug-containing polymeric formulation of the present invention comprises at least rapamycin. Rapamycin, also referred to as sirolimus, is a macrocyclic triene antibiotic produced by *Streptomyces hygroscopicus* as disclosed in U.S. Pat. No. 3,929,992. It has been found that rapamycin, among other things, inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls. Rapamycin reduces vascular hyperplasia by antagonizing smooth muscle proliferation in response to mitogenic signals that are released during an angioplasty-induced injury. Inhibition of growth factor and cytokine mediated smooth muscle proliferation at the late G1 phase of the cell cycle is believed to be the domain mechanism of action of rapamycin. However, rapamycin is also known to prevent T-cell proliferation and differentiation when administered systematically, and it therefore can be used as an immunosuppressant for preventing graft rejection.

The at least one therapeutic agent as described hereinabove is encapsulated into at least one biocompatible polymer, which provides structural support for the therapeutic agent, functions as a carrier matrix therefore, and controls the release thereof. The at least one biocompatible polymer of the present invention may be any suitable biocompatible polymer or any suitable mixture of polymers, including, but not limited to: biocompatible addition polymers and biocompatible condensation polymers. Further, the at least one biocompatible polymer of the present invention may either be biostable or biodegradable, and it may even comprise a polymer blends of a biostable polymer and a biodegradable polymer.

Biostable polymers that are suitable for use in this invention include, but are not limited to: polyurethane, silicones, polyesters, polyolefins, polyamides, poly(esteramide), polycaprolactam, polyimide, polyvinyl chloride, polyvinyl methyl ether, polyvinyl alcohol, acrylic polymers and copolymers, polyacrylonitrile; polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof; and mixtures and copolymers of the foregoing.

Biodegradable polymers that can be used in this invention include, but are not limited to: polylactic acid (PLA), polyglycolic acid (PGA), copolymers of lactic acid and glycolic acid (PLGA), polycaprolactone, polyphosphoester, polyorthoester, poly(hydroxy butyrate), poly(dioxanone), poly(hydroxy valerate), poly(hydroxy butyrate-co-valerate), poly(glycolide-co-trimethylene carbonate), polyanhydrides, poly(ester-amide), polyphosphazene, poly(phosphoester-urethane), poly(amino acids), biopolymeric molecules such as fibrin, fibrinogen, cellulose, starch, collagen and hyaluronic acid, and mixtures and copolymers of the foregoing.

Preferably, but not necessarily, the at least one biocompatible polymer of the present invention is a biodegradable polymer selected from the group consisting of PLA, PGA, PLGA, and mixtures thereof. More preferably, the polymeric material used by the present invention comprises the PLGA copolymer. The PLA, PGA, or PLGA polymers may be any of D-, L- and D-/L-configuration.

The at least one biocompatible polymer of the present invention may form a substantially continuous polymeric matrix with the at least one therapeutic agent encapsulated therein. The substantially continuous polymeric matrix can either constitute at least a portion of an implantable medical device or form a coating over at least a portion of the implantable medical device. Various implantable medical devices can be formed or coated by the drug-containing polymeric composition of the present invention to effectuate controlled local drug delivery. For example, such implantable medical devices may be selected from stents, stent grafts, anastomosis devices, vascular grafts, vascular patches, AV shunts, catheters, guide wires, balloons, filters, etc.

Alternatively, the at least one biocompatible polymer of the present invention may form polymeric particles with the at least one therapeutic agent encapsulated therein. The polymeric particles may have any suitable sizes (e.g., from about 1 nm to about 1 mm in average diameter) and shapes (e.g., sphere, ellipsoid, etc.). Preferably, but not necessarily, the at least one biocompatible polymer of the present invention forms nano- and/or micro-particles that are suitable for injection. The term "nano-particles" or "micro-particles" is used throughout the present invention to denote carrier structures that are biocompatible and have sufficient resistance to chemical and/or physical destruction by the environment of use such that a sufficient amount of the nano-particles and/or micro-particles remain substantially intact after injection into a target site in the arterial wall. Typically, the nano-particles of the present invention have sizes ranging from about 1 nm to about 1000 nm, with sizes from about 100 nm to about 500 nm being more preferred. The micro-particles of the present invention have sizes ranging from about 1 µm to about 1000 µm, with sizes from about 10 µm to about 200 µm being more preferred. The pharmacologically active agent as described hereinabove is loaded within and/or on the surfaces of the nano-particles and/or micro-particles.

In a particularly preferred embodiment of the present invention, the at least one therapeutic agent are first formed into crystalline particles of desired sizes, which are then encapsulated into the at least one biocompatible polymer. Preferably, but not necessarily, the crystalline particles of the therapeutic agent have an average particle size ranging from about 50 nm to about 50 µm, and more preferably from about 100 nm to about 200 nm.

In order to retain the physical properties of the drug-containing devices (polymer film or coating integrity, etc), it may be necessary to reduce the particle size of the therapeutic agents. Smaller drug particle size will also provide different drug formulation and processing options, without affecting the processing efficiency. Crystalline drug particles with the desired particle sizes can be readily formed by several different processes, as described hereinafter.

Nanotechnology provides new and enhanced particle formulation processes and offers a wide range of options for achieving drug particles in the micro- and nano-size range. Some of the new developments in nanotechnology have successfully achieved particle engineering by using molecular scaffolds like dendrimers (polyvalent molecules) and fullerenes (i.e., C-60 "bucky balls"). The small-size drug particles that can be formed by using nanotechnology are particularly useful for formulating poorly soluble drugs, since the reduced drug particle sizes significantly improve the bioavailability of such drugs, by providing higher surface area and accelerating dissolution and absorption of such drugs by the body.

Further, conventional techniques, such as milling (either dry or wet), supercritical extraction, spray drying, precipitation, and recrystallization, can also be used to prepare micro- and nano-size drug particles.

Milling is a well-established micronization technique for obtaining desired micro- and nano-size drug particles (either dry or suspended in liquid) with well controlled size distribution.

Dry milling can be used to obtain particle size below about 50 microns. Various dry milling methods, such as jet milling, high-speed mixer milling, planetary milling, fluid energy jet milling, and ball milling, can be used to grind drug particles to about 1 micron. Milling is a relatively less expensive, faster, and easily scalable method, in comparison with other methods. Micronization occurs by particle collision (e.g., particle-particle or collisions among the particles and the grinding media like balls, pins, or beads) in various vessel configurations that may be stationary or shaken, rolled, or spun. These processes may involve compressed steam, compressed nitrogen, or compressed air. Process variables include air pressure used for grinding, time in the grinding zone and the feed rate.

Wet milling can be used to form solid drug particles below 1 micron to 80-150 nm with well defined size distribution. Bead milling uses rotating agitator disks to move microsized grinding beads (50 microns to 3.0 mm) in an enclosed grinding chamber to produce particles as small as 0.1 micron. Another wet-milling system (NanoCrystal™ System developed by Elan Drug Delivery) used for poorly water-soluble drugs generates particles sized in the 100-200 nm range.

Supercritical fluids (SCF) can also be used to form small-size drug particles, by extracting solvents from dissolved drugs while drug-containing droplets are sprayed out of a nozzle. The anti-solvent used for extraction is typically supercritical carbon dioxide, and the solvent(s) is typically water, ethanol, methanol, or isopropyl alcohol. No solvent is used if the drug is readily soluble in compressed carbon dioxide. In this event, the drug-containing supercritical carbon dioxide simply is sprayed into a depressurized vessel. The particle-formation rate can be controlled by changing the pressure, temperature, and spray rate. The particle size is determined mainly by the size of the droplet and the choice of the SCF. Dissolving the same drug into two different solvents may result in two different particle sizes. Particle sizes ranges typically in the range of about 100 nm. Crystalline morphology of the drug particles is retained by careful control over the small period of time when a drug comes out of solution and forms the particles.

Spray-drying technology is similar to the SCF approach, except that instead of using a SCF to remove the solvent(s), the solvent(s) is removed by a controlled drying process. A drug and excipient formulation is dissolved in a solvent or a mixture of two or more solvents. The solution is then sprayed through a nozzle, forming very fine droplets, which are passed down a drying chamber at either elevated or reduced temperatures. A drying gas, such as nitrogen, causes the solvent(s) to precipitate from the droplets, resulting in dry drug particles. One particularly preferred spray-drying method uses a multichamber spray dryer to produce porous microspheres. The chambers are arranged in series, so that the particles can be dried sequentially at different temperatures. The crystallinity of the drug particles is retained by controlling the chamber temperatures and the drying conditions.

Spray drying can generate particles with mean size ranges from 700 nm to 2-3 microns. Spray drying can be used with either water-soluble or insoluble drugs.

Precipitation is another technique that can be used to form small-sized drug particles from solution. One precipitation technique specifically uses low-frequency sonication to speed up the precipitation process, by producing a homogenous shear field inside the vessel. A drug-containing solution is introduced into a vessel sitting on a magnetic plate oscillating at frequencies typically around 60 Hz. The frequency facilitates the precipitation of the drug particles, which can then be dried or filtered. Precipitation can also be achieved by pH shift, by using a different solvent, or by changing the temperature. The oscillation frequency, the volume, and the manner in which the precipitation is achieved can be readily adjusted to form drug particles of the desired particle sizes. The particle size achieved by precipitation is typically in the range of 400 to 600 nm.

Another approach for forming the small-size drug particles of the present invention is a two-step process, which includes a first step where a drug or a drug-polymer combination is dissolved in an organic solvent to produce drug-containing polymeric particles by micro-precipitation in an aqueous solvent under controlled conditions, and a second step where high-pressure homogenization or milling is carried out to reduce the particle size of the drug-containing polymeric particles, followed by coating the particles with a surfactant for stabilization. Particle sizes of the drug-containing polymeric particles so formed can be controlled by temperature and time range, and the typical particle size ranges from about 100 nm to about 1 micron.

The crystalline properties of the drugs can also be readily controlled. The process works well with drugs that are poorly soluble in water.

Re-crystallization process is a continuous process in which high-pressure impinging streams are used to bring two reactants of insoluble materials together. When the reactants impinge on each other for a very short reaction time, particles start to form with desired sizes.

If the particle sizes of the crystalline drug particles as provided are already suitable for forming a polymeric composition that can be subsequently used to form or coat a drug-eluting implantable medical device or drug-eluting micro- and/or nano-particles, then such crystalline drug particles can be directly used for forming the polymeric composition. However, if the particle sizes of the crystalline drug particles as provided are too large, the above-described methods can be readily used, either separately or in combination, to reduce the particles size down to a desired size range.

The drug-containing polymeric composition of the present invention can be formed by various methods that effectively encapsulate the small-size crystalline drug particles, as described hereinabove, into at least one biocompatible polymer as described hereinabove, provided that during and after the processing steps of such methods, at least a portion of the crystalline particles remain crystalline. Preferably more than 50%, more preferably more than 75%, and most preferably more than 90% of the crystalline particles remain crystalline during and after the processing steps of such methods.

In a preferred but not necessary embodiment of the present invention, the crystalline particles are encapsulated into the at least one biocompatible polymer by a process that uses a polymeric solution. Specifically, the polymeric solution comprises the at least one biocompatible polymer as dissolved in a solvent system, which may comprise a single solvent or multiple solvents, provided that the crystalline particles of the at least one therapeutic agent are insoluble in such a solvent system. In this manner, the crystalline particles can retain their crystallinity even after mixing with the polymeric solution, and the mixture can then be processed, i.e., to remove all or substantially all of the solvent(s), to form the drug-containing polymeric composition with the crystalline particles of therapeutic agent encapsulated therein. Solvent selection is therefore important for the present invention, to ensure that the biocompatible polymer is properly dissolved in the polymeric solution, without adversely affecting the crystallinity of the therapeutic agent.

Sirolimus, which is also referred to as rapamycin, is a crystalline powder with a melting point of about 180° C. It is highly soluble in organic solvents, such as dioxane, chloroform, acetone, acetonitrile, benzyl alcohol, but is insoluble in water. A two-step process can therefore be used, in which the first step is to dissolve sirolimus in an organic solvent, such as acetone, and to produce sirolimus particles by micro-precipitation in an aqueous solvent, and the second step is to further mill or homogenize the sirolimus particles, thereby reducing the particle sizes of the sirolimus particles to a desired range. Alternatively, small-size sirolimus particles can be directly formed as an aqueous dispersion of NanoCrystal™ particles using the wet milling method.

After formation of a polymeric solution (e.g., PLGA in dioxane), the small-size sirolimus crystalline particles are mixed with the polymeric solution to form a mixture, followed by solvent removal, thereby forming a drug-containing polymeric composition with small-size crystalline particles of sirolimus encapsulated therein.

Tranilast is a crystalline powder with a melting point of about 210° C. It is soluble in dimethyl sulfoxide (DMSO), but not soluble in other solvents such as methylene chloride. This drug can be added to a polymer solution that contains a polymer (e.g., PLGA) dissolved in a solvent such as methylene chloride, so that tranilast remains insoluble in the polymer solution, thereby retaining its crystalline structure. After mixing tranilast with the polymeric solution, the solvent (e.g., methylene chloride) is removed from the mixture, thereby forming a drug-containing polymeric composition with the crystalline particles of tranilast encapsulated therein.

The drug/polymeric solution mixture can be either formed into or coated over at least a portion of an implantable medical device before the solvent removal. In this manner, a substantially continuous biocompatible matrix is formed after the solvent removal, which constitutes at least a portion of the implantable medical device, or a coating over such an implantable medical device, with the crystalline particles of the therapeutic agent encapsulated therein.

Alternatively, the crystalline drug particles are first encapsulated individually by a protective coating layer that is not dissolvable in the polymeric solution, before mixed with the polymeric solution. In this manner, the crystalline drug particles, being individually encapsulated and protected by the protective material layer, will retain their crystallinity in the polymeric solution, regardless of whether the drug particle itself is soluble or insoluble in the polymeric solution. In other words, the protective material layer forms a barrier for the drug particles to prevent the drug particles from being dissolved by the solvent(s) contained in the polymeric solution, thereby preserving the crystalline morphology of the drug particles.

Micro-encapsulation is a process in which tiny particles or droplets are individually encapsulated by protective coating layers to form small capsules with many useful properties. The material inside the microcapsule is usually known as the core, which is surrounded by a wall, sometimes referred to as a shell, coating, or membrane. Most of the microcapsules have diameters between a few micrometers and a few millimeters. The core of a microcapsule may be a single crystal, a jagged particle, an emulsion, a suspension of solids, or a suspension of smaller microcapsules.

There are several reasons for preparing micro-encapsulations. In some cases, the core must be isolated from its environment, as in isolating an active ingredient from the deteriorating effects of oxygen, retarding evaporation of a volatile core, improving the handling and flow properties of a sticky material, or isolating a reactive core from chemical attack. In other cases, the objective is not to isolate the core completely but to control the rate at which it leaves the microcapsule, as in the controlled release of drugs. It may also be as simple as masking the taste or odor of the core, or as complex as increasing the selectivity of an adsorption or extraction process.

There are several physical and chemical methods to prepare microcapsules. Some of the physical methods include pan coating, air-suspension coating, spray drying, spinning disk and extrusion-spheronization.

Pan coating process is widely used in the pharmaceutical industry and is amongst the oldest industrial procedure for forming small, coated particles or tablets. In general, the particles are tumbled in a pan or other device while the coating material is applied slowly.

Air-suspension coating of particles by solutions or melts gives better control and flexibility. The particles are coated while suspended in an upward-moving air stream. They are supported by a perforated plate having different patterns of holes inside and outside a cylindrical insert. Sufficient air is permitted to rise through the outer annular space to fluidize the settling particles. Most of the rising air (usually heated) flows inside the cylinder, causing the particles to rise rapidly. At the top, as the air stream diverges and slows, they settle back onto the outer bed and move downward to repeat the cycle. The particles pass through the inner cylinder many times in a few minutes.

Some of the chemical methods that can be used for forming micro-capsules include interfacial polymerization, in-situ polymerization and matrix polymerization. In interfacial polymerization, two reactants meet at the interface and react rapidly in a polycondensation reaction, and condensed polymer walls form instantaneously at the interface. In-situ polymerization can be carried out on a particle surface by direct polymerization of a single monomer, and the coating so formed is uniform and the thickness can range from 0.2 to 75 µm. Matrix polymerization is similar to spray drying, where the core material is imbedded in a polymeric matrix during formation of the particles, but the solidification of the matrix is caused by a chemical reaction.

Alternatively, the drug-containing polymeric particles as described hereinabove can be formed by spray-drying a polymeric solution onto the small-sized crystalline particles of the therapeutic agent. Spray drying serves as a microencapsulation technique when an active material is suspended in a melt or polymer solution and becomes trapped in the dried particle. The main advantage of this method is its ability to handle labile materials, due to the short contact time in the dryer. For example, sirolimus can be coated with a water soluble polymer such as hydroxypropyl cellulose or polyvinyl pyrrolidone. Dilute polymer solutions can be prepared in water, and desired amount of sirolimus can be added to the polymer solution. Since sirolimus is insoluble in water, it will retain its crystallinity. Upon spray drying the polymeric solution at drying temperatures sufficiently high for evaporating water, a thin polymer coating layer is formed on each drug particle, without altering the crystalline structure of the sirolimus drug particles.

Spinning disk atomization process, on the other hand, uses an emulsion or suspension containing the drug prepared with a solution or melt of the coating material. The emulsion or suspension is fed to a rotating or spinning disc surface and forms a thin wetted layer that breaks up into airborne droplets, due to surface tension forces as the disc rotates. For example, crystalline particles of a therapeutic agent are first mixed with a polymeric solution or melt, and the mixture is then dropped onto a spinning disk that is operated at a temperature ranging from about 80° C. to about 135° C. and a rotating speed ranging from about 5,000 revolutions per minute (RPM) to about 10,000 RPM. The disk diameter can be from about 2 to 6 inches. The resulting microcapsules are typically spherical, with particle sizes ranging from a few microns to a few hundred microns. The coating materials can be low-melting-point waxy polymeric materials, such as poly (ethylene glycol) or monoglyceride-succinic anhydride, and can be dissolved in solvents, such as acetone, that can evaporate very rapidly. This process permits use of high viscosity coating materials and can achieve a high loading dose of the drug.

In a still further embodiment of the present invention, the polymeric particles as described hereinabove can be formed by a melt extrusion and compounding process, which is also referred to as an extrusion/spheronization process. Extrusion/spheronization is a multi-step process that can be used to make uniformly sized spherical drug-containing particles for controlled drug release applications. The main advantage of this process is the ability to incorporate high levels of active ingredients without producing excessively large particles. The main steps of the extrusion/spheronization process include: (1) dry mixing of ingredients to achieve a homogenous powder dispersion; (2) extrusion of the powder dispersion to form rod-shaped particles of uniform diameters; (3) spheronization of the rod-shaped particles into spherical particles; (4) drying of the spherical particles to achieve a desired final moisture content; and (5) screening or filtering of the dried spherical particles to achieve a desired narrow size distribution. The extrusion/spheronization process can be used in the present invention to form drug-containing polymeric particles of desired drug release profile (e.g., either an immediate release profile or a controlled release profile), depending on the polymer used to coat the drug particles. Further, each polymeric particle can contain two or more active drugs. Alternatively, two or more active ingredients that may potentially interact with one another in an undesired manner (i.e., incompatible) can be encapsulated into separate polymeric particles and thereby isolated from one another by the polymeric coating materials.

The process of extrusion/spheronization can be used to increase the bulk density, improve the flow properties, and reduce the problems of dusting usually associated with low-density, finely divided powders of active ingredients and excipients.

Specifically, a biocompatible polymer, which has a lower melting temperature than the therapeutic agent to be encapsulated, is melted, and the melted polymer is then mixed with the crystalline particle of the therapeutic agent to form a molten mixture. Since the therapeutic agent has a higher melting temperature than the polymer, the crystallinity of the therapeutic particles is not affected by mixing with the melted polymer. Subsequently, the molten mixture is extruded into a desired shape, e.g., a rod, disc, sphere, etc., and then cooled to below the melting temperature of the biocompatible polymer, thereby forming a solidified structure that comprises a substantially continuous polymeric matrix with the crystalline particles of the therapeutic agent encapsulated therein. The solidified structure can be treated by various techniques, such as, for example, crushing, chopping, mincing, grinding, milling, spheronization and/or pulverizing, to form polymeric particles of the desired sizes and shapes.

Any biocompatible polymer or polymer blends that has a melting temperature lower than that of the therapeutic agent can be used in the above-described melt compounding process. For example, polycaprolactone, which has a processing temperature of about 100° C., can be used for melt compounding with rapamycin (i.e., sirolimus), which has a melting temperature of about 180° C. For another example, polydioxanone, which has a processing temperature of about 100 to 110° C., can be used for melt compounding with tranilast, which has a melting temperature of about 210° C. Poly(glycolide-caprolactone) copolymer (65/35), which has a processing temperature of about 120° C., can be used for melt compounding with cladribine, which has a melting temperature of about 220° C. Poly(caprolactone-dioxanone) copolymer (95/5), which has a processing temperature of about 80 to 100° C., can be used for melt compounding with sabeluzole, which has a melting temperature of about 110° C.

In a still further embodiment of the present invention, the drug-containing polymeric composition as described hereinabove can be formed by a slow cooling process, during which the at least therapeutic agent is converted from an amorphous phase to a crystalline phase. For example, a precursor composition, which comprises at least one therapeutic agent encapsulated in at least one biocompatible polymer, can be first formed from a polymeric solution that comprises at least one biocompatible polymer and at least one therapeutic agent, both dissolved in a solvent system comprising one or more solvents. The precursor composition formed from such a polymeric solution comprises the therapeutic agent in the unstable, amorphous phase. The precursor composition is then treated, either by annealing to an elevated temperature (e.g., 100° C.) or by adding an anti-solvent at room temperature or an elevated temperature (e.g., 50° C.), followed by very slow cooling (e.g., from 100° C. to 30° C. in 30 to 60 minutes) of such composition. Slow cooling will thermodynamically allow the drug molecule to change from the amorphous phase to the crystalline phase.

The above-described methods can be used either independently, or in combination with one another, to form the drug-containing polymeric composition of the present invention.

While specific embodiments of the present invention are described and illustrated hereinabove, it is clear that a person ordinarily skilled in the art can readily modify such specific embodiments consistent with the descriptions provided herein. It should therefore be recognized that the present invention is not limited to the specific embodiments illustrated hereinabove, but rather extends in utility to any other modification, variation, application, and embodiment, and accordingly all such other modifications, variations, applications, and embodiments are to be regarded as being within the spirit and scope of the invention.

What is claimed is:

1. A drug-containing polymeric composition comprising rapamycin in crystalline form encapsulated in at least one biocompatible polymer, wherein at least 95 percent of the rapamycin in said composition is crystalline, the crystals being in the range from about 100 nanometers to about 200 nanometers.

* * * * *